United States Patent [19]

Murakami

[11] Patent Number: 5,792,945
[45] Date of Patent: Aug. 11, 1998

[54] APPARATUS FOR DETERMINING THE AMOUNT OF A SURFACTANT DISSOLVED IN A SOLUTION

[75] Inventor: Toru Murakami, Tokyo, Japan

[73] Assignee: NEC Corporation, Tokyo, Japan

[21] Appl. No.: 603,774

[22] Filed: Feb. 20, 1996

[30] Foreign Application Priority Data

Feb. 17, 1995 [JP] Japan .................... 7-029166

[51] Int. Cl.⁶ ............................................ G01N 13/00
[52] U.S. Cl. ........................................ 73/64.48; 118/402
[58] Field of Search ............................. 73/53.01, 64.48, 73/64.49; 118/402

[56] References Cited

U.S. PATENT DOCUMENTS

| 3,780,569 | 12/1973 | Graham | 74/64.4 |
|---|---|---|---|
| 4,192,842 | 3/1980 | Kimura et al. | 264/298 |
| 4,397,839 | 8/1983 | Tanaka | 424/95 |
| 4,413,506 | 11/1983 | Abraham et al. | 73/64.4 |
| 4,599,969 | 7/1986 | Barraud et al. | 118/402 X |
| 5,006,374 | 4/1991 | Wakayama et al. | 118/402 X |
| 5,021,268 | 6/1991 | Khanarian et al. | 427/430.1 |
| 5,044,308 | 9/1991 | Mojtabaj | 118/402 |
| 5,149,374 | 9/1992 | Miyuadera et al. | 118/691 |
| 5,558,855 | 9/1996 | Quay | 424/9.5 |
| 5,567,413 | 10/1996 | Klaveness et al. | 424/9.51 |

Primary Examiner—Hezron E. Williams
Assistant Examiner—Jay L. Politzer
Attorney, Agent, or Firm—Young & Thompson

[57] ABSTRACT

An apparatus for determining the amount of any chemical substance exhibiting a surface activity. A monomolecule film including a surface active substance exhibiting a surface activity is formed on a surface of a surface active substance solution in which the surface active substance is dissolved. Subsequently, a surface pressure of the monomolecule film is measured in order to find a concentration of the surface active substance where a content of the surface active substance is defined by the concentration of the surface active substance and the amount of the solution.

5 Claims, 2 Drawing Sheets

APPARATUS FOR DETERMINING THE AMOUNT OF A SURFACTANT DISSOLVED IN A SOLUTION

BACKGROUND OF THE INVENTION

The present invention relates to an apparatus for determining an amount of a surfactant dissolved in a solution.

The surface active agent is a typical chemical substance which exhibits a surface activity. A plurality of typical conventional methods for analyzing the surface active agent are disclosed in Kodansya Scientific 1982. "analysis and examination of surface active agent".

A first conventional method for analyzing the surface active agent is as follows. Long-chain sulfate and long-chain sulfate such as alkylbenzene sulfate, dodecyl sulfate, alkylpolyoxyethylene sulfate, alkenyl sulfonate and alkyl sulfonate can act as an anionic surface active agent. Such an anionic surface active agent forms water-soluble Methylene Blue and complex and dissolved in chloroform, which shows a blue color. A sufficient amount of cationic surface active agent is added into this system, then a complex salt of the anionic and cationic surface active agents is generated whereby Methylene Blue comes free. This phenomenon is utilized to determine the anionic surface active agent.

A second conventional method for analyzing the surface active agent is a Methylene Blue separate phase back titration. Methylene Blue acid solution acting as a basis dye is added as a separation phase indicator into a anionic surface active agent solution, and further either chloroform or benzene is added as a solvent into the anionic surface active agent solution. An excess amount of a cationic surface active agent solution is added so that the excess amount of the cationic surface active agent is subjected to a back titration by an anionic surface active agent standard solution.

A third conventional method for analyzing the surface active agent is carried out by utilizing the same chemical reaction as the first method described above in order to determine cationic surface active agents such as amine fatty acid, quaternary ammonium salt, alkylpyridium salt.

A fourth conventional method for analyzing the surface active agent is as follows. Bromophenol is used as a separation phase indicator. Dichloroethane is used as a separation phase solvent. The anionic surface active agent solution standard solution is subjected to a titration by the cationic surface active agent until the bottom solvent layer is colored in blue in order to directly determine the cationic surface active agent.

A fifth conventional method for analyzing the surface active agent is phosphorus wolframate volumetric analysis. Long-chain quaternary ammonium salt shows a quantitative reaction to phosphorus wolframate whereby a water-insoluble complex salt deposit is generated. Quaternary ammonium slat is bonded to azosulfonic acid based coloring matter such as Congo Red, and Methyl Orange, for which reason quaternary ammonium salt shows no acidic color in acid solution. In the titration by phosphorus wolframate, at a equivalence point quaternary ammonium slat first shows a certain acidic color. This phenomenon is utilized to subject the cationic surface active agent acid solution to a direct titration with phosphorus wolframate by use of Congo Red indicator so that the absolute concentration of the cationic surface active agent is determined on the basis of the titration value and the weight of the generated complex salt deposit.

A sixth conventional method for analyzing the surface active agent is a sodium tetraphenylboron complex salt back titration method. Hydrochloric acid solution is used in which polyoxyethylene based non-ionic surface active agent is dissolved. In the solution, an excess amount of sodium tetraphenylboron complex salt is added in the presence of $Ba^{2+}$ to form a complex salt deposit. Methyl Orange is used as an indicator to subject the excess sodium tetraphenylboron complex salt to a back titration with a quaternary ammonium salt standard solution so that the absolute concentration of the non-ionic surface active agent is determined on the basis of the titration value and the weight of the generated complex salt deposit.

A seventh conventional method for analyzing the surface active agent is a phosphorus wolframate method. An amphoteric surface active agent such as betaine is subjected to a direct titration with phosphorus wolframate by using benzopurpurin 4B as an indicator to thereby find a concentration of the amphoteric surface active agent.

Subsequently, a plurality of conventional microanalysis for surface active agents included in river water, service water, sewage water and drain will hereinafter be described. The microanalysis is not only used for determination of the surface active agent in environment but also essential for biodegradation measurement of the surface active agent.

A first conventional microanalysis is carried out by organic solvent extraction of an anionic surface active agent as Methylene Blue active substance for coloimetrie.

A second conventional microanalysis is a determination of a non-ionic active surface agent in bismuth iodine method (Wickbold). The non-ionic surface active agent is concentrated into an ethyl acetate layer by gas stripping. Ethyl acetate is removed and a residual non-ionic surface active agent is dissolved in water for subsequent addition of improved Dragendorff reagent to cause a deposition of non-ionic surface active agent. This deposit is separated to wash the same with ice acetic acid before the washed non-ionic surface active agent is then dissolved in an ammonium tartrate solution. Bismuth in the solution is subjected to a potentiometric titration with pyrrolidine thiocarbmart solution at pH value of 4–5.

A third conventional microanalysis is a cobalt thiocyanic acid method. Ethyleneoxide based non-ionic surface active agent and cobalt ammonium thiocyanic acid are used to form a complex. The complex is extracted on a benzene layer for determination of the non-ionic surface active agent in an absorptiometric method.

A fourth conventional microanalysis is carried out as follows. Cationic surface active agent is isolated and anionic surface active agent is removed before a complex of the cationic surface active agent and disulfine blue is extracted for coloimetric.

A fifth conventional microanalysis is a method for determination of amphoteric surface active agent by Orange II. The amphoteric surface active agent exhibits a cationic property at a pH value not more than isoelectric point, and thus the amphoteric surface active agent and Orange II of anionic property quantitatively form a complex compound. The complex compound is extracted with chloroform before the determination in an absorptiometric method at 485 nm.

In another method, liquid chromatography is applicable to anionic, cationic, amphoteric and non-ionic surface active agents. The liquid chromotography allows a separation analysis without any previous chemical treatment. There are four methods for analyzing the surface active agent utilizing the liquid chromatography.

A first liquid chromatography analyzing method is an analysis for an anionic surface active agent such as sodium alkyl sulfate. An OSD chemical bonding silica-gel of chemical-bonded octadecylsilane is used as a filler. A solvent of 85% of methanol and 15% of water is added with a sodium chloride to form an eluent. A reversed phase chromatography is carried out using the filler and the eluent to measure alkyl distribution of the anionic surface active agent.

A second liquid chromatography analyzing method is an analysis for a cationic surface active agent, alkylbenzenedimethylammonium and alkylpyridinium slat by utilizing a reversed chromatography, wherein styrene-divinylbenzene based porous polymer is sued as a column filler and wherein methanol is added with hydrochloride, fulfonic acid, sodium perchlorate, perchloric acid to form an eluent.

A third liquid chromatography analyzing method is carried out by determination of the amphoteric surface active agent such as 2-hydroxy-3-sulfopropyl-dimethylalkyl ammonium and sulfopropyl-dimethylalkyl ammonium is determined by a reversed phase chromatography with an eluent of 80% of methanol and 20% of water and an OSD chemical bonding silica-gel of chemical-bonded octadecylsilane as a filler.

A fourth liquid chromatography analyzing method is carried out as follows. A silica-gel is used as a filler. There are used as an eluent 34% of carbon tetrachloride and 66% of isooctane, 40% of chloroform, 11% of dioxane and 49% of hexane, and chloroform, methanol and diisopropylether to carry out a gradient extraction method so that the non-ionic surface active agent, monoacylglycerin, diacylglycerin and triacylglycerin are subjected to separation analysis.

In addition to the above, the gas chromatography method and the protein determination method have been used for analysis of the surface active agent.

The conventional analyzing method for the surface active agent requires relatively complicated operations and apparatus for the liquid and gas chromatography and spectrophotometer. It is further required to select columns of the chemical analyzing methods and chromatography to match the kinds of the surface active agents. Furthermore, it is required to use an organic solvent such as chloroform which causes ozone destruction.

The conventional protein determination method requires relatively complicated operations and spectrophotometer. In an UV method, the determination of the surface active agent is influenced by a substance which absorbs an ultraviolet ray.

SUMMARY OF THE INVENTION

Accordingly, it is an object of the present invention to provide a novel method for determination of the amount of a surface active substance.

It is a further object of the present invention to provide a simple method for determining the amount of a surfactant.

It is a further more object of the present invention to provide a method for determination of the amount of a surfactant, which is free from any time-consuming procedure.

It is another object of the present invention to provide a novel apparatus for determination of the amount of a surfactant without using any surface active agent.

It is a further another object of the present invention to provide a simple apparatus for determination of amount of a surfactant.

It is yet another object of the present invention to provide a apparatus for determination of the amount of a surfactant, which is free from any time-consuming procedure.

The above and other objects, features and advantages of the present invention will be apparent from the following descriptions.

The present invention provides a method for determination of amount of any chemical substance exhibiting a surface activity. The method comprises the following steps. A monomolecule film including a surface active substance exhibiting a surface activity is formed on a surface of a surface active substance solution in which the surface active substance is dissolved. Subsequently, a surface pressure of the monomolecule film is measured in order to find a concentration of the surface active substance where a content of the surface active substance is defined by the concentration of the surface active substance and the amount of the solution.

In the above case, the surface active substance dispersed in micelle in the surface active substance solution may be allowed to move naturally to a surface of the surface active substance solution to thereby form the monomolecule film of the surface active substance on the surface.

Alternatively, a monomolecule film developing solution is dropped onto a surface of the surface active substance solution in which the surface active substance is dissolved or dispersed to thereby form the monomolecule film of the surface active substance on the surface.

The above surface active substance is defined as a substance which is classified into any one of any anionic surface active agents, any cationic surface active agents, any nonionic surface active agents, any amphoteric surface active agents or any proteins.

The present invention further provides an apparatus for determination of amount of a surface active substance comprising the following elements. A trough is provided, which has at least a cell which contains a surface active substance solution in which a surface active substance is dissolved or dispersed. A measuring unit is provided over the trough for measuring a surface tension of the monomolecule film. A computing unit is electrically coupled to at least the measuring unit for receiving information of the surface tension measured from the measuring unit in order to compute a concentration of the surface active substance and then find a content of the surface active substance on the basis of the concentration computed.

A dropping unit may optionally be provided over the trough for dropping a monomolecule film developing solution onto a surface of the surface active substance solution in order to form the monomolecule film on the surface of the surface active substance solution.

BRIEF DESCRIPTIONS OF THE DRAWINGS

Preferred embodiments of the present invention will be described in detail with reference to the accompanying drawings.

DISCLOSURE OF THE INVENTIONS

Figure 1:
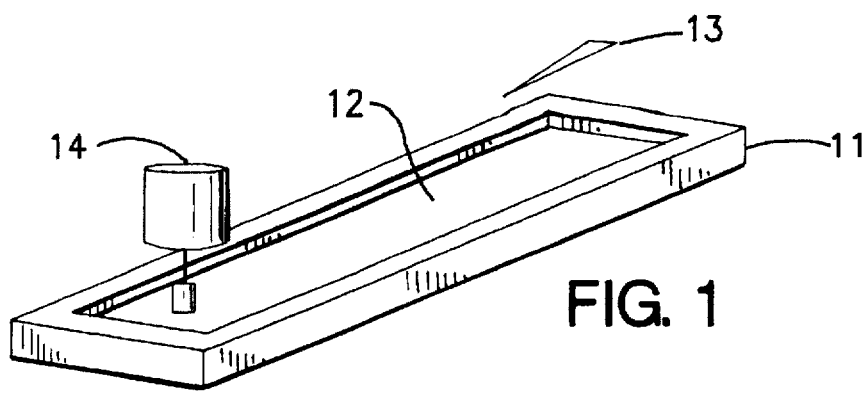
FIG. 1 is a perspective view illustrative of an apparatus for forming a monomolecule film having an amphoteric property and subsequent measuring a surface tension thereof according to the present invention.

The present invention provides a method for determining an amount of any chemical substance exhibiting a surface activity. The method comprises the following steps. A monomolecule film including a surface active substance exhibiting a surface activity is formed on a surface of a surface active substance solution in which the surface active substance is dissolved. Subsequently, a surface tension of the monomolecule film is measured in order to find a concentration of the surface active substance where a content of the surface active substance is defined by the concentration of the surface active substance and the amount of the solution.

In the above case, the surface active substance dispersed in micelle in the surface active substance solution may be allowed to move naturally to a surface of the surface active substance solution to thereby form the monomolecule film of the surface active substance on the surface.

Alternatively, a monomolecule film developing solution is dropped onto a surface of the surface active substance solution in which the surface active substance is dissolved or dispersed to thereby form the monomolecule film of the surface active substance on the surface.

The above surface active substance may be any one of any anionic surface active agents or any cationic surface active agents, any non-ionic surface active agents, any amphoteric surface active agents any proteins. The anionic surface active agent may, for example, be sodium dodecylsulfate or alkylbenzenesulfonate. The cationic surface active agent may, for example, be aliphatic amine salt or quaternary ammonium salt. The non-ionic surface active agent may, for example, be any one of polyoxyethylene based non-ionic surface active agents. The amphoteric surface active agent may, for example, be betaine.

The surface tension of the monomolecule film having an amphoteric property be measured with a surface tension meter.

The surface active substance solution may be a buffer solution including N-2-hydroxyethylpiperazine-N'-2-ethane sulfuric acid, where the ion strength is 0.1 and pH value is 7.45 as well as the surface active substance such as sodium dodecylsulfate dissolved in the buffer solution.

The surface active substance solution also may be a buffer solution including N-2-hydroxyethylpiperazine-N'-2-ethane sulfuric acid, where the ion strength is 0.1 and pH value is 7.45 as well as the surface active substance such as sodium dodecylsulfate dissolved in the buffer solution, and wherein the monomolecule film development solution includes L-α-di-myristylphosphatizircoline.

The surface active substance solution also may be a buffer solution including N-2-hydroxyethylpiperazine-N'-2-ethane sulfuric acid, where the ion strength is 0.1 and pH value is 7.45 as well as the surface active substance such as beef serum albumin dissolved in the buffer solution, and wherein the monomolecule film development solution includes an arachidinic acid.

The present invention further provides an apparatus for determining an amount of a surface active substance comprising the following elements. A trough is provided, which has at least a cell which contains a surface active substance solution. A measuring unit is provided over the trough for measuring a surface tension of the monomolecule film. A computing unit being electrically coupled to at least the measuring unit for receiving information of the surface tension measured from the measuring unit in order to compute a concentration of the surface active substance and then find a content of the surface active substance on the basis of the concentration computed.

A dropping unit may optionally be provided over the trough for dropping a monomolecule film developing solution onto a surface of the surface active substance solution in order to form the monomolecule film on the surface of the surface active substance solution.

A movable partition plate may also be provided over the trough for partitioning the surface active substance solution into a primary part and a subordinate part, wherein the surface tension of the monomolecule film formed on the primary part is measured. A partition plate controller may also be coupled to the movable partition plate for controlling movements of the movable partition plate so as to set a surface area of the primary part at a predetermined value. In this case, a computing unit computes a position of the movable partition plate on the basis of the predetermined value of the surface area of the primary part, and the partition plate controller is electrically coupled to the computing unit for receiving information of the position computed from the computing unit.

The measuring unit may comprise a surface tensiometer for measuring a surface tension of the monomolecule film, wherein the computing unit computes the surface tension on the basis of the measurements by the surface tensiometer.

A movable stage may be provided under the trough for mechanically supporting and moving the trough in a horizontal plane, and a stage controller may be coupled to the stage for controlling movement of the stage. The stage controller is also electrically coupled to the computing unit for receiving information of the movement of the stage. In this case, the trough has a rectangular shape and the movable stage moves the trough on the basis of X-Y coordinates. Alternatively, the trough has a circular shape and has a plurality of cells which are circumferentially aligned and different monomolecule films are formed, and in which the movable stage rotates the trough.

EXAMPLES

Example 1

A first embodiment of the present invention directed to a method for determining in the amount of the surface active substance will be described with reference to a first example as follows.

A surface active agent solution 12 is introduced in a trough 11 so that a surface tension of a monomolecule film formed on a surface of the surface active agent solution 12 is measured by a surface tensiometer 14. There was used a buffer solution including N-2-hydroxyethylpiperazine-N'-2-ethane sulfuric acid, where the ion strength is 0.1 and the pH value is 7.45. In the example, 0.01 mM (millimolar), 0.1 mM, and 1 mM of sodium dodecylsulfate are dissolved in the buffer solution.

10 ml of a sodium dodecylsulfate solution in which 0.01 mM of sodium dodecylsulfate is dissolved in injected into the trough 11 having a size of 30 mm×150 mm, wherein the trough 11 contains the buffer solution. A part of sodium dodecylsulfate dissolved in the solution is moved to a surface of the solution to form a monomolecule film of sodium dodecylsulfate. A surface tension of the monomolecule film of sodium dodecylsulfate was measured by the surface tensiometer. It was confirmed that the surface tension is gradually increased from 0 mN/m (milli Newton/meter) to 1.8 mN/m and then comes into an equilibrium state.

10 ml of a sodium dodecylsulfate solution in which 0.1 mM of sodium dodecylsulfate is dissolved is injected into the trough 11 having a size of 30 mm×150 mm, wherein the trough 11 contains the buffer solution. A part of sodium dodecylsulfate dissolved in the solution is moved to a surface of eh solution to form a monomolecule film of sodium dodecylsulfate. A surface tension of the monomolecule film of sodium dodecylsulfate was measured by the surface tensiometer. It was confirmed that the surface tension is gradually increased from 0 mN/m to 2.8 mN/m and then comes into an equilibrium state.

10 ml of a sodium dodecylsulfate solution in which 1 mM of sodium dodecylsulfate is dissolved is injected into the trough 11 having a size of 30 mm×150 mm, wherein the trough 11 contains the buffer solution. A part of sodium dodecylsulfate dissolved in the solution is moved to a surface of the solution to form a monomolecule film of sodium dodecylsulfate. A surface tension of the monomolecule film of sodium dodecylsulfate was measured by the surface tensiometer. It was confirmed that the surface tension is gradually increased from 0 mN/m beyond 8.3 mN/m and then comes into an equilibrium state.

TABLE 1

| Sodium dodecylsulfate (µM) | 0 | 100 | 1000 |
|---|---|---|---|
| surface tension (mN/m) | 1.8 | 2.8 | >8.3 |

From the results of the measurement of the surface tension, it can be understood that the surface tension of the monomolecule film of sodium dodecylsulfate depends upon the concentration of sodium dodecylsulfate dissolved in the buffer solution. Analytical curves were previously prepare by measuring surface tension of a plurality of different sodium dodecylsulfate solutions which respectively have different concentrations already known of sodium dodecylsulfate. An unknown concentration of sodium dodecylsulfate dissolved in the buffer solution can be found on the basis of the prepared analytical curves. The concentration of sodium dodecylsulfate dissolved in the buffer solution can be determined according to the above method.

The above surface active substance may be any one of any anionic surface active agents, any cationic surface active agents, any non-ionic surface active agents, any amphoteric surface active agents or any proteins. The anionic surface active agent may, for example, be sodium dodecylsulfate or alkylbenzenesulfonate. The cationic surface active agent may, for example, be aliphatic amine salt or quaternary ammonium salt. The non-ionic surface active agent may, for example, be any one of polyoxyethylene based non-ionic surface active agents. The amphoteric surface active agent may, for example, be betaine.

If a plurality of different surface active agents are dissolved in the buffer solution, a total amount of the different surface active agents can be found by conversion into amount of the standard surface active agent such as sodium dodecylsulfate.

Example 2

A second embodiment of the present invention directed to a method for determining the amount of the surface active substance will be described with reference to a second example as follows.

A surface active agent solution 12 is introduced in a trough 11 so that a surface tension of a monomolecule film formed on a surface of the surface active agent solution 12 is measured by a surface tensiometer 14. There was used a buffer solution including N-2-hydroxyethylpiperazine-N'-2-ethane sulfuric acid, where the ion strength is .1 and pH value is 7.45. In this example 0 µM, 0.1 µM, 1 µM, and 10 µM of sodium dodecylsulfate are dissolved in the buffer solution. As a monomolecule film development solution 13, there was used a monomolecule film development solution into which 1 mM of L-α-dimyristylphosphatizircoline is dissolved.

10 ml of a sodium dodecylsulfate solution in which 0 µM of sodium dodecylsulfate is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 11 µl of the monomolecule film developing solution 13 was dropped onto the buffer solution to form a monomolecule film. A surface tension of the monomolecule film of sodium dodecylsulfate was measured by the surface tensiometer 14. It was confirmed that the surface tension was gradually increased from 0 mN/m to 0.5 mN/m and then comes into an equilibrium state.

10 ml of a sodium dodecylsulfate solution in which 0.1 µM of sodium dodecylsulfate is dissolved i injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 11 µl of the monomolecule film developing solution 13 was dropped onto the buffer solution to form a monomolecule film. A surface tension of the monomolecule film of sodium dodecylsulfate was measured by the surface tensiometer 14. It was confirmed that the surface tension was gradually increased from 0 mN/m to 1.2 mN/m and then comes into an equilibrium state.

10 ml of a sodium dodecylsulfate solution in which 1 µM of sodium dodecylsulfate is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 11 µl of the monomolecule film developing solution 13 was dropped onto the buffer solution to form a monomolecule film. A surface tension of the monomolecule film of sodium dodecylsulfate was measured by the surface tensiometer 14. It was confirmed that the surface tension was gradually increased from 0 mN/m to 2.8 mN/m and then comes into an equilibrium state.

10 ml of a sodium dodecylsulfate solution in which 10 µM of sodium dodecylsulfate is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 11 μl of the monomolecule film developing solution 13 was dropped onto the buffer solution to form a monomolecule film. A surface tension of the monomolecule film of sodium dodecylsulfate was measured by the surface tensiometer 14. It was confirmed that the surface tension was gradually increased from 0 mN/m to 7.5 mN/m and then comes into an equilibrium state.

TABLE 2

| Sodium dodecylsulfate (μM) | 0 | 0.1 | 1 | 10 |
|---|---|---|---|---|
| surface tension (mN/m) | 0.5 | 1.2 | 2.8 | 7.5 |

From the results of the measurement of the surface tension, it can be understood that the surface tension of the monomolecule film of sodium dodecylsulfate depends upon the concentration of sodium dodecylsulfate dissolved in the buffer solution. Analytical curves were previously prepared by measuring surface tensions of a plurality of different sodium dodecylsulfate solutions which respectively have different concentrations already known of sodium dodecylsulfate. An unknown concentration of sodium dodecylsulfate dissolved in the buffer solution can be found on the basis of the prepared analytical curves. The concentration of sodium dodecylsulfate dissolved in the buffer solution can be determined according to the above method.

The above surface active substance may be any one of any anionic surface active agents, any cationic surface active agents, any non-ionic surface active agents, any amphoteric surface active agents or any proteins. The anionic surface active agent may, for example, be sodium dodecylsulfate or alkylbenzenesulfonate. The cationic surface active agent may, for example, be aliphatic amine salt or quaternary ammonium salt. The non-ionic surface active agent may, for example, be any one of polyoxyethylene based non-ionic surface active agents. The amphoteric surface active agent may, for example, be betaine.

If a plurality of different surface active agents are dissolved in the buffer solution, a total amount of the different surface active agents can be found by conversion into amount of the standard surface active agent such as sodium dodecylsulfate.

Example 3

A third example according to the present invention directed to a method for determination in the amount of the surface active substance will be described.

A surface active agent solution 12 is introduced in a trough 11 so that a surface tension of a monomolecule film formed on a surface of the surface active agent solution 12 is measured by a surface tensiometer 14. There was used a buffer solution including N-2-hydroxyethylpiperazine-N'-2-ethane sulfuric acid, where the ion strength is 0.1 and pH value is 7.45. In this example 0 μg/ml, 0.1 μg/ml, 1 μg/ml, 10 μg/ml and 100 μg/ml of beef serum albumin are dissolved in the buffer solution. As a monomolecule film development solution 13, there was used a monomolecule film development solution into which 1 mM of arachidinic acid is dissolved.

10 ml of a beef serum albumin solution in which 0 μg/ml of beef serum albumin is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 20 μl of the monomolecule film developing solution 13, into which 1 mM of arachidinic acid is dissolved, was dropped onto the buffer solution to form a monomolecule film. A surface tension of the monomolecule film of beef serum albumin was measured by the surface tensiometer 14. It was confirmed that the surface tension was gradually increased from 0 mN/m to 0.5 mN/m and then comes into an equilibrium state.

10 ml of a beef serum albumin solution in which 0.1 μg/ml of beef serum albumin is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 20 μl of the monomolecule film developing solution 13, into which 1 mM of arachidinic acid is dissolved, was dropped onto the buffer solution to form a monomolecule film. A surface tension of the monomolecule film of beef serum albumin was measured by the surface tensiometer 14. It was confirmed that the surface tension was gradually increased from 0 mN/m to 0.9 mN/m and ten comes into an equilibrium state.

10 ml of a beef serum albumin solution in which 10 μg/ml of beef serum albumin is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 20 μl of the monomolecule film developing solution 13, into which 1 mM of arachidinic acid is dissolved, was dropped onto the buffer solution to form a monomolecule film. A surface tension of the monomolecule film of beef serum albumin was measured by the surface tensiometer 14. It was confirmed that the surface tension was gradually increased from 0 mN/m to 1.7 mN/m and then comes into an equilibrium state.

10 ml of a beef serum albumin solution in which 10 μg/ml of beef serum albumin is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 20 μl of the monomolecule film developing solution 13, into which 1 mM of arachidinic acid is dissolved, was dropped onto the buffer solution to form a monomolecule film. A surface tension of the monomolecule film of beef serum albumin was measured by the surface tensiometer 14. It was confirmed that the surface tension was gradually increased from 0 mN/m to 2.8 mN/m and ten comes into an equilibrium state.

10 ml of a beef serum albumin solution in which 100 μg/ml of beef serum albumin is dissolved is injected into the trough 11 having a size of 30 mm×150 mm, wherein the trough 11 contains the buffer solution. A surface tension of a surface of the buffer solution was measured by the surface tensiometer. It was confirmed that the surface tension is gradually increased from 0 mN/m to 1.8 mN/m and then comes into an equilibrium state. The surface tensiometer 14 was compensated so as to indicate 0 mN/m. In this state, 20 µl of the monomolecule film developing solution 13, into which 1 mM of arachidinic acid is dissolved, was dropped onto the buffer solution to form a monomolecule film. A surface tension of the monomolecule film of beef serum albumin was measured by the surface tensiometer 14. It was confirmed that the surface tension was gradually increased from 0 mN/m to 8.2 mN/m and then comes into an equilibrium state.

TABLE 3

| beef serum albumin (µM) | 0 | 0.1 | 1 | 10 | 100 |
|---|---|---|---|---|---|
| surface tension (mN/m) | 0.5 | 0.9 | 1.7 | 2.8 | 7.5 |

From the results of the measurement of the surface tension, it can be understood that the surface tension of the monomolecule film of beef serum albumin depends upon the concentration of beef serum albumin dissolve din the buffer solution. Analytical curves were previously prepared by measuring surface tension of a plurality of different beef serum albumin solutions which respectively have different concentrations already known of sodium dodecylsulfate. An unknown concentration of beef serum albumin dissolved in the buffer solution can be found on the basis of the prepared analytical curves. The concentration of beef serum albumin dissolved in the buffer solution can be determined according to the above method.

The above surface active substance may be any one of any anionic surface active agents, any cationic surface active agents, any non-ionic surface active agents, any amphoteric surface active agents or any proteins. The anionic surface active agent may, for example, be sodium dodecylsulfate or alkylbenzenesulfonate. The cationic surface active agent may, for example, be aliphatic amine salt or quaternary ammonium salt. The non-ionic surface active agent may, for example, be any one of polyoxyethylene based non-ionic surface active agents. The amphoteric surface active agent may, for example, be betaine.

If a plurality of different surface active agents are dissolved in the buffer solution, a total amount of the different surface active agents can be found by conversion into amount of the standard surface active agent such as beef serum albumin.

Example 4

A fourth example according to the present invention directed to a method for determination in the amount of the surface active substance will be described.

A surface active agent solution 12 is introduced in a trough 11 so that a surface tension of a monomolecule film formed on a surface of the surface active agent solution 12 is measured by a surface tensiometer 14. There was used a buffer solution including N-2-hydroxyethylpiperazine-N'-2-ethane sulfuric acid, where the ion strength is 0.1 and pH value is 7.45 as well as no surface active agent is dissolved in the buffer solution. In place of the above buffer solution free of any surface active agent, river waters #1 and #2 were also used, in which any surface active agent might be dissolved. As a monomolecule film development solution 13, there was used a monomolecule film development solution into which 1 mM of L-α-dipalmytylphosphatizircoline is dissolved.

The surface tensiometer 14 was compensated so as to indicate 0 mN/m. Thereafter, 11 µl of the monomolecule film developing solution 13, into which 1 mM of arachidinic acid was dissolved, was dropped onto the buffer solution to form a monomolecule film. A surface tension of the monomolecule film was measured by the surface tensiometer 14. It was confirmed that the surface tension was gradually increased from 0 mN/m to 0.6 mN/m and then comes into an equilibrium state.

The surface tensiometer 14 was compensated so as to indicate 0 mN/m. Thereafter, 11 µl of the monomolecule film developing solution 13, into which 1 mM of sodium dodecylsulfate was dissolved, was dropped onto the river water #1 to form a monomolecule film. A surface tension of the monomolecule film was measured by the surface tensiometer 14. It was confirmed that the surface tension was gradually increased from 0 mN/m to 4.8 mN/m and then comes into an equilibrium state.

The surface tensiometer 14 was compensated so as to indicate 0 mN/m. Thereafter, 11 µl of the monomolecule film developing solution 13, into which 1 mM of sodium dodecylsulfate was dissolved, was dropped onto the river water #2 to form a monomolecule film. A surface tension of the monomolecule film was measured by the surface tensiometer 14. It was confirmed that the surface tension was gradually increased from 0 mN/m to 1.5 mN/m and then comes into an equilibrium state.

TABLE 4

| solution | HEPES | river water #1 | river water #2 |
|---|---|---|---|
| surface tension (mN/m) | 0.6 | 4.8 | 1.5 | where HEPES means the buffer solution including N-2-hydroxyethylpiperazine-N'-2-ethane sulfuric acid.

By comparing Table 4 with Table 2, it can be understood that about in the conversion of sodium dodecylsulfate, 0.1 µM of the surface active agent is dissolved in the river water #1 and in the river water #2 more than 1 µM of the surface active agent is dissolved.

A third embodiment of the present invention will be described with reference to seventh to ninth examples. This embodiment is directed to an apparatus for both determining the amount of the surface active substance and evaluating the toxicity of chemical substances.

Example 5

Figure 2:
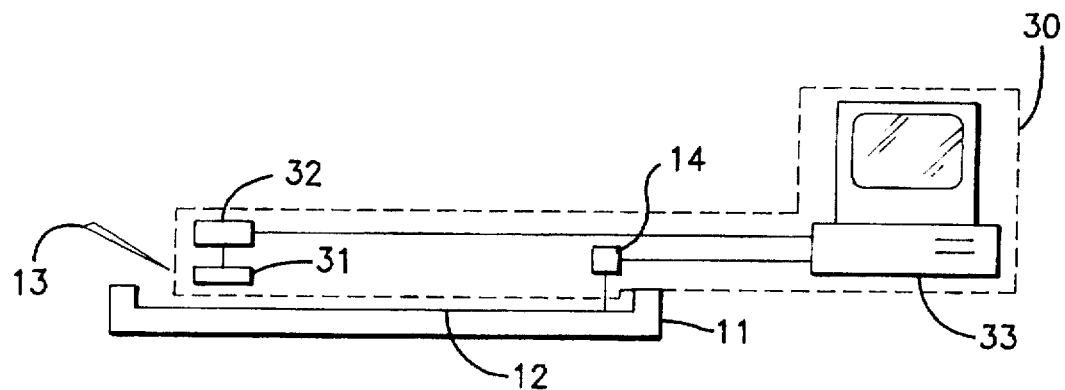
FIG. 2 is a schematic view illustrative of apparatuses for determination of amount of a surface active substance in one example according to the present invention.

An apparatus for both determination in the amount of the surface active substance comprises a trough 11 and a surface tension controller 30. FIG. 2 schematically illustrates the apparatus in this embodiment. The trough 11 receives the surface active substance solution 12 on which a monomolecule film having an amphoteric property is formed by dropping a monomolecule film development solution onto the surface thereof. The surface tension controller 30 is provided to set, at a constant value, an initial surface tension of the monomolecule film of the surface active agent at a time when the surface tension measurement is commenced. The surface tension controller 30 has a partition plate 31 which is positioned over the surface active substance solution 12. The surface area of the monomolecule film of the surface active agent formed on the surface of the surface active substance solution 12 is defined by the position of the partition plate 31. The position of the partition plate 31 is adjusted by a partition plate positioning controller 32. The partition plate positioning controller 32 is mechanically connected to the partition plate 31 for adjusting the position of the partition plate 31. The partition plate positioning controller 32 is electrically connected to a control unit 33 for receiving electrical information about the surface tension of the monomolecule film of the surface active agent formed on the surface of the surface active substance solution 12 so as to adjust the position of the partition plate 31 on the basis of the information about the surface tension from the control unit 33. The control unit 33 is electrically connected to a surface tensiometer 14 which is positioned over the surface active substance solution 12 and adjusted to measure a surface tension of the monomolecule film of the surface active agent formed on the surface of the surface active substance solution 12. The control unit 33 receives, from the surface tensiometer 14, electrical information about the surface tension of the monomolecule film, which has ben measured by the surface tensiometer 14. The monomolecule film development solution 13 is dropped onto a surface of the surface active substance solution 12 to form the monomolecule film.

As described above, the surface tension controller 30 is provided to control at a constant value the initial surface tension of the monomolecule film of the surface active agent at an initial time of the measurement thereof in order to improve accuracy in the measurement of the surface pressure of the monomolecule film. This allows a correct and accurate determination of the amount of the surface active substance dissolved or dispersed in the surface active substance solution.

Example 6

Figure 3:
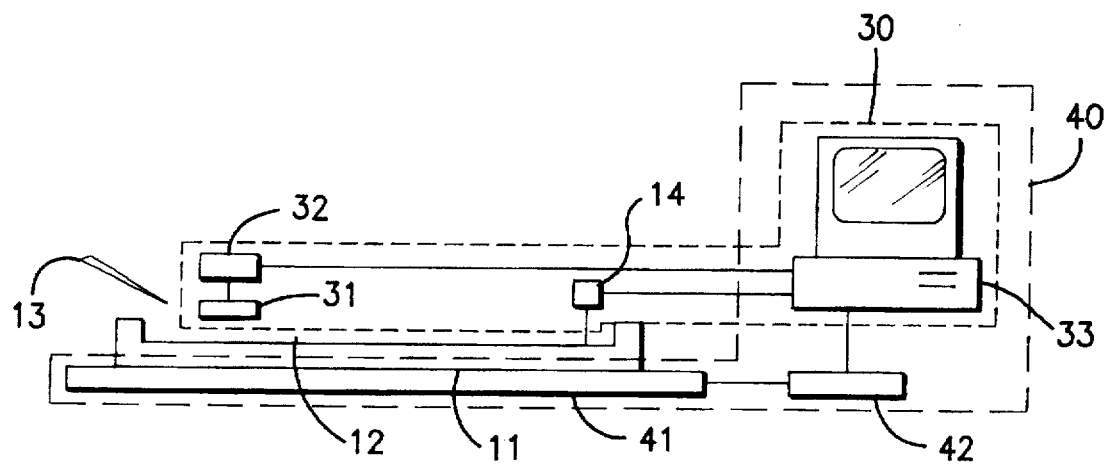
FIG. 3 is a schematic view illustrative of apparatuses for determination of amount of a surface active substance in another example according to the present invention.

An apparatus for both determining the amount of the surface active substance and evaluating the toxicity of chemical substances comprises not only a trough 11 and a surface tension controller 30 but also a stage control system 40. FIG. 3 schematically illustrates the apparatus in this embodiment. The trough 11 receives the surface active substance solution 12 on which a monomolecule film of the surface active agent is formed by dropping a monomolecule film development solution onto the surface thereof. The surface tension controller 30 is provided to set, at a constant value, an initial surface tension of the monomolecule film of the surface active agent at a time when the surface tension measurement is commenced. The surface tension controller 30 has a partition plate 31 which is positioned over the surface active substance solution 12. The surface area of the monomolecule film the surface active agent formed on the surface of the surface active substance solution 12 is defined by the position of the partition plate 31. The position of the partition plate 31 is adjusted by a partition plate positioning controller 32. The partition plate positioning controller 32 is electrically connected to a control unit 33 for receiving electrical information about the surface tension of the monomolecule film having an amphoteric property formed on the surface of the surface active substance solution 12 so as to adjust the position of the partition plate 31 on the basis of the information about the surface tension from the control unit 23. The control unit 23 is electrically connected to a surface tensiometer 14 which is positioned over the surface active substance solution 12 and adjusted to measure a surface tension of the monomolecule film of the surface active agent formed on the surface of the surface active substance solution 12. The control unit 33 receives, from the surface tensiometer 14, electrical information about the surface tension of the monomolecule film, which has been measured by the surface tensiometer 14. The monomolecule film development solution 13 is dropped onto a surface of the surface active substance solution 12 to form the monomolecule film. The stage control system 40 comprises the above control unit 33, an X-Y stage 41 and an X-Y stage controller 42. The X-Y stage 41 is provided to support the trough 11 so that the trough 11 is placed on the X-Y stage 41. The X-Y stage, on which the trough 11 receiving the surface active substance solution 12 is placed, is adjusted to move the trough 11 in a horizontal plane (e.g., perpendicular to the page) along X-axis and Y-axis which are perpendicular to each other. The X-Y stage may be mechanically connected to the X-Y stage controller 42 so that the X-Y stage can be mechanically moved by the X-Y stage controller 42. Otherwise, the X-Y stage may be electrically connected to the X-Y stage controller 42 for receiving electrical signals as instructions of what amounts of distances the trough 11 should be moved in the X and Y directions so that the X-Y stage can move by itself on the basis of the electrical signals.

As described above, the surface tension controller 30 and the stage control system 40 are provided to control at a constant value the initial surface tension of the monomolecule film of the surface active agent at an initial time of the measurement thereof in order to improve accuracy in the measurement of the surface tension of the monomolecule film. This allows a correct and accurate determination of the amount of the surface active substance dissolved or dispersed in the surface active substance solution.

Example 7

Figure 5:
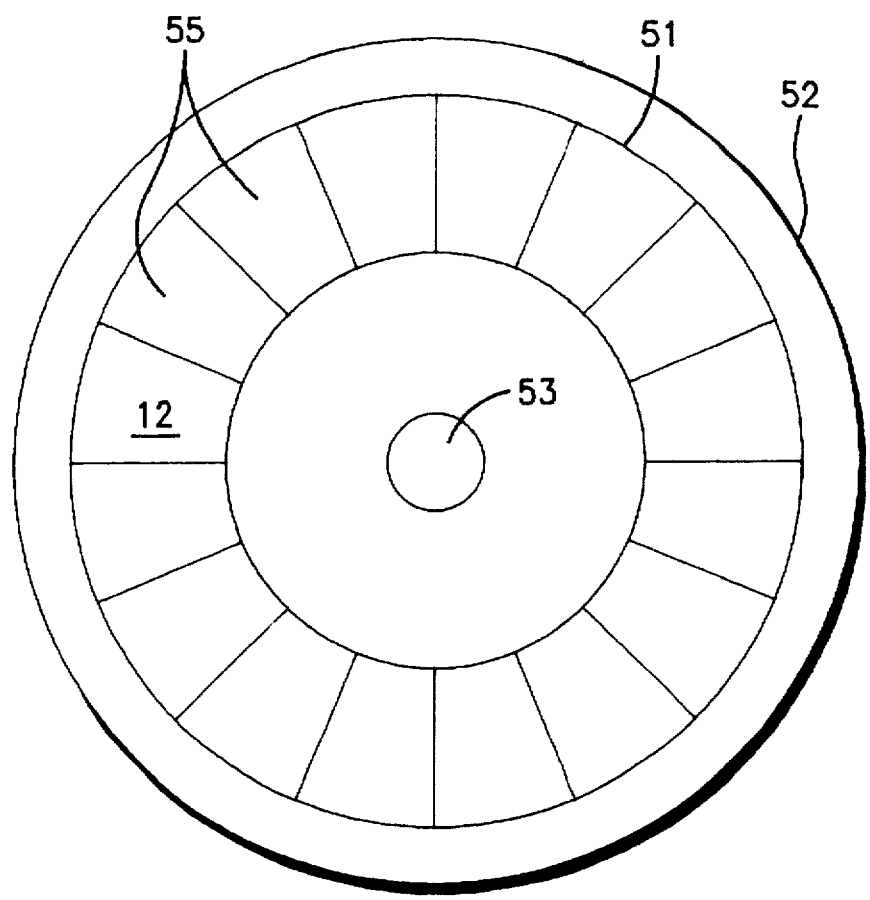
FIG. 5 is a plan view illustrative of a circulation trough, a circulation stage and a stage controller to be used according to the present invention.
Figure 4:
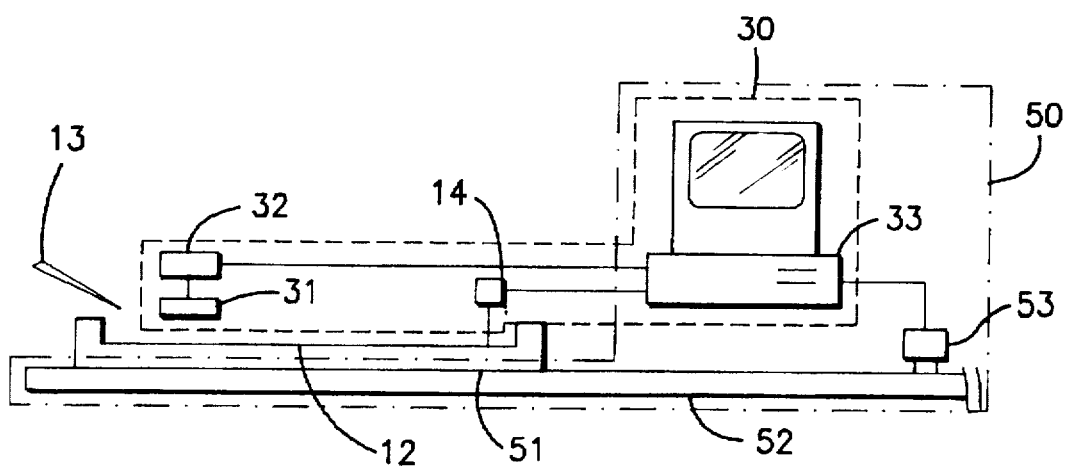
FIG. 4 is a schematic view illustrative of apparatuses for determination of amount of a surface active substance in still another example according to the present invention.

An apparatus for both determining the amount of the surface active substance and evaluating the toxicity of chemical substances comprises not only a circulation trough 51 and a surface tension controller 30 but also a stage control system 50. FIG. 4 schematically illustrates the apparatus in this embodiment. FIG. 5 is a plan view illustrative of a further embodiment of a circulation trough 51, a circulation stage 52 and a circulation stage controller 53. The circulation trough 51 has a plurality of cells, each of which receives the surface active substance solution 12 on which a monomolecule film of the surface active agent is formed by dropping a monomolecule film development solution onto the surface thereof. The surface tension controller 30 is provided to set, at a constant value, an initial surface tension of the monomolecule film having an amphoteric property at a time when the surface tension measurement is commenced. The surface tension controller 30 has a partition plate 31 which is positioned over the surface active substance solution 12. The surface area of the monomolecule film of the surface active agent formed on the surface of the surface active substance solution 12 is defined by the position of the partition plate 31. The position of the partition plate 31 is adjusted by a partition plate positioning controller 32. The partition plate positioning controller 32 is mechanically connected to the partition plate 31 for adjusting the position of the partition plate 31. The partition plate positioning controller 32 is electrically connected to a control unit 33 for receiving electrical information about the surface tension of the monomolecule film of the surface active agent formed on the surface of the surface active substance solution 12 so as to adjust the position of the partition plate 31 on the basis of the information about the surface tension from the control unit 33. The control unit 33 is electrically connected to a surface tensiometer 14 which is positioned over the surface active substance solution 12 and adjusted to measure a surface tension of the monomolecule film of the surface active agent formed on the surface of the surface active substance solution 12. The control unit 33 receives, from the surface tensiometer 14, electrical information about the surface tension of the monomolecule film, which has been measured by the surface tensiometer 14. The monomolecule film development solution 13 is dropped onto a surface of the surface active substance solution 12 to form the monomolecule film. The stage control system 50 comprises the above control unit 33, circulation stage 52 and circulation stage controller 53. The circulation stage 52 is provided to support the circulation trough 51 so that the circulation trough 51 is placed on the circulation stage 52. The circulation stage, on which the circulation trough 51 receiving the surface active substance solution 12 is placed, is adjusted to rotate the circulation trough 51 in a horizontal plane. The circulation stage 52 may be mechanically connected to the circulation stage controller 53 so that the circulation stage 52 can be mechanically rotated by the circulation stage controller 53. Otherwise, the circulation stage 52 may be electrically connected to the circulation stage controller 53 for receiving electrical signals as instructions of what amounts of distances the circulation trough 51 should be rotated in the horizontal plane so that the circulation stage 52 can rotate by itself on the basis of the electrical signals.

As described above, the circulation trough 51 has a plurality of cells 55 which are individually designed to receive different surface active substance solutions in order to allow short-time determinations of the amount of the different surface active substance or short-time evaluations on the toxicity of different chemical substances dissolved or dispersed in the surface active substance solutions. The surface tension controller 30 and the stage control system 50 are provided to control at a constant value the initial surface tension of the monomolecule film having an amphoteric property at an initial time of the measurement thereof in order to improve the accuracy of the measurement of the surface tension of the monomolecule film. This allows a correct and accurate determination of the amount of the surface active substance or a correct and accurate evaluation on the toxicity of chemical substance dissolved or dispersed in the surface active substance solution.

Whereas modifications of the present invention will be apparent to a person having ordinary skill in the art, to which the invention pertains, it is to be understood that embodiments as shown and described by way of illustrations are by no means intended to be considered in a limiting sense. Accordingly, it is to be intended to cover all modifications which fall within the spirit and scope of the following claims directed to the subject mater of the present invention.

What is claimed is:

1. An apparatus for determination of an amount of a surface active substance, comprising:

a trough having at least a cell which contains a surface active substance solution in which a surface active substance exhibiting a surface activity is dissolved;

a movable stage provided under said trough for mechanically supporting and moving said trough in a horizontal plane;

a stage controller coupled to said stage for controlling movement of said stage;

a dropping means provided over said trough for dropping a monomolecule film developing solution onto a surface of said surface active substance solution in order to form a monomolecule film on said surface of said surface active substance solution;

at least a movable partition plate provided over said trough for partitioning said surface active substance solution into a primary part and a subordinate part;

a partition plate controller coupled to said movable partition plate for controlling movements of said movable partition plate;

a measuring means provided over said trough for measuring a surface tension of said monomolecule film on said primary part of said surface active substance solution;

a computing means electrically coupled to at least said measuring means for receiving information of said surface tension measured in order to compute a concentration of said surface active substance and then find a content of said surface active substance on the basis of said computed concentration, wherein said computing means computes a position of said movable partition plate, and wherein said partition plate controller is electrically coupled to said computing means for receiving information of said computed position to move said movable partition plate in order to adjust a surface area of said primary part so that before an initiation of a subsequent surface tension measurement, said surface tension of said monomolecule film is controlled at a predetermined value.

2. The apparatus as claimed in claim 1, wherein said measuring means comprises a surface tensiometer.

3. The apparatus as claimed in claim 1, wherein said stage controller is electrically coupled to said computing means for receiving information of said movement of said stage.

4. The apparatus as claimed in claim 1, wherein said trough has a rectangular shape and wherein said movable stage moves said trough on the basis of X-Y coordinates.

5. The apparatus as claimed in claim 1, wherein said trough has a circular shape and has a plurality of cells which are circumferentially aligned and different monomolecule films are formed, and that said movable stage rotates said trough.

* * * * *